(12) United States Patent
Lucy

(10) Patent No.: US 7,411,107 B2
(45) Date of Patent: Aug. 12, 2008

(54) ALKENE SEPARATION PROCESS

(75) Inventor: Andrew Richard Lucy, Brough (GB)

(73) Assignee: BP Chemicals Limited, Middlesex (GB)

( * ) Notice: Subject to any disclaimer, the term of this patent is extended or adjusted under 35 U.S.C. 154(b) by 478 days.

(21) Appl. No.: 10/502,940

(22) PCT Filed: Feb. 12, 2003

(86) PCT No.: PCT/GB03/00686

§ 371 (c)(1),
(2), (4) Date: Jul. 29, 2004

(87) PCT Pub. No.: WO03/074454

PCT Pub. Date: Sep. 12, 2003

(65) Prior Publication Data

US 2005/0148791 A1    Jul. 7, 2005

(30) Foreign Application Priority Data

Mar. 4, 2002    (GB) ................................. 0205016.9

(51) Int. Cl.
*C07C 5/327* (2006.01)
*C07C 27/00* (2006.01)
*C07C 67/05* (2006.01)
*C07B 53/00* (2006.01)

(52) U.S. Cl. .................... 585/658; 585/324; 585/809; 585/843; 585/844; 585/845; 585/848; 585/850; 585/856; 560/241; 560/214.1; 560/243; 560/245; 562/548; 562/549; 562/606

(58) Field of Classification Search ................ 585/651, 585/652, 809, 843, 844, 845, 848, 850, 856, 585/654, 658; 560/241, 241.1, 243, 245; 562/548, 549, 606

See application file for complete search history.

(56) References Cited

U.S. PATENT DOCUMENTS

| 6,040,474 A | 3/2000 | Jobson et al. |
| 6,143,921 A | 11/2000 | Karim et al. |
| 6,476,261 B2 * | 11/2002 | Ellis et al. .................... 562/606 |
| 6,518,476 B1 * | 2/2003 | Culp et al. .................... 585/655 |

FOREIGN PATENT DOCUMENTS

| EP | 0 985 656 A1 | 3/2000 |
| WO | WO 00/37399 | 6/2000 |
| WO | WO 01/90042 A1 | 11/2001 |
| WO | WO 01/90043 A1 | 11/2001 |

* cited by examiner

*Primary Examiner*—Glenn Caldarola
*Assistant Examiner*—In Suk Bullock
(74) *Attorney, Agent, or Firm*—Nixon & Vanderhye

(57) ABSTRACT

A process for the oxidation of a $C_2$ to $C_4$ alkane to produce the corresponding alkene and carboxylic acid which process comprises separation of the alkene from a mixture of the alkene, the alkane and oxygen by absorption in a metallic salt solution, and recovery of an alkene-rich stream from the metallic salt solution. Integrated processes for the production of alkyl carboxylate and alkenyl carboxylate, which processes comprise oxidation of a $C_2$ to $C_4$ alkane to produce the corresponding alkene and carboxylic acid, separation of the alkene from a mixture of the alkene, the alkane and oxygen by absorption in a metallic salt solution, and recovery of an alkene-rich stream from the metallic salt solution for use in production of alkyl carboxylate or alkenyl carboxylate.

45 Claims, 1 Drawing Sheet

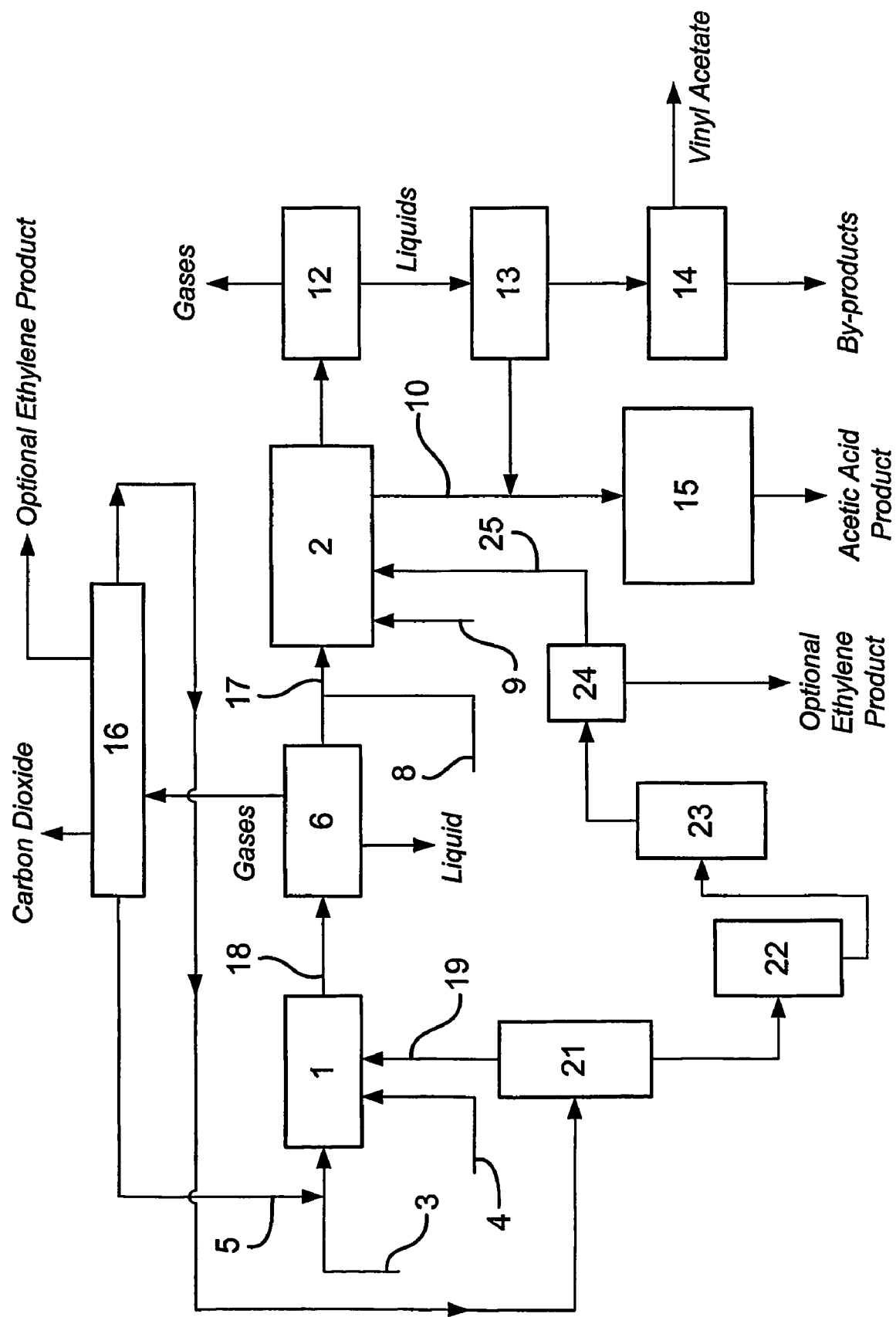

ALKENE SEPARATION PROCESS

This application is the U.S. National Phase of International Application PCT/GB03/00686, filed Feb. 12, 2003, which designated the U.S.

The present invention relates to the separation of alkenes from gas mixtures comprising said alkenes, alkanes and oxygen and, in particular, to the separation of ethylene from a mixture of ethylene, ethane and oxygen by absorption in a metallic salt solution.

The present invention also relates to the use of the separation process in (a) hydrocarbon oxidation processes such as the oxidation of a $C_2$ to $C_4$ alkane to produce the corresponding alkene and carboxylic acid and (b) in integrated processes in which the alkene and carboxylic acid produced from a hydrocarbon oxidation process are further used as reactants.

Ethylene and acetic acid may be produced by the catalytic oxidation of ethane. In a typical oxidation process to produce ethylene and acetic acid, ethane, oxygen and optionally ethylene and/or water are introduced into a reactor. The reactants are contacted with an oxidation catalyst such as a molybdenum/niobium/vanadium containing catalyst and react to produce an outlet stream comprising ethylene (either as product or unreacted feed), acetic acid, unreacted ethane and unreacted oxygen. The outlet stream is removed from the reactor, condensed and separated into a gaseous stream and a liquid stream. The gaseous stream comprising ethane, ethylene and oxygen may be further purified to obtain ethylene therefrom. The liquid stream comprising acetic acid and water may be further purified.

It is known that the separation of ethylene from hydrocarbons such as ethane may be carried out by distillative processes such as cryogenic distillation and adsorption techniques such as pressure swing adsorption and reactive adsorption. In addition, where the alkane/alkene gas mixture comprises oxygen, such as the gas mixture produced by the oxydehydrogenation of ethane to ethylene as described, for example, in EP-A-0 262 264, the oxygen is traditionally removed prior to separation of the alkene from the alkane. If the oxygen is not removed prior to the separation of the hydrocarbons, the separation process can concentrate the oxygen such that the oxygen-containing stream becomes flammable or explosive.

EP-A-0 943 595 describes a process for separating an alkene such as ethylene from a gas mixture comprising the alkene and an alkane such as ethane by a pressure swing absorption process comprising the steps of passing the gas mixture through a type A zeolite having exchangeable sodium and potassium ions and regenerating the zeolite to produce an alkene-enriched gas. Such a pressure swing adsorption system is mechanically complex and a single adsorption cycle gives only a small enhancement of ethylene concentration. No mention is made of the separation of alkenes from gas mixtures comprising alkenes, alkanes and oxygen.

WO 00/37399 describes a process for the auto-thermal cracking of paraffinic hydrocarbons with oxygen in which process the product stream comprises ethylene, propene, butene and carbon monoxide. Ethylene and propene are separated from the product stream by contacting the product stream with a solution of a metallic salt capable of selectively absorbing the ethylene and propene and recovering the ethylene and/or propene from the metallic salt. Prior to treatment with the metallic salt solution, the product stream is treated to remove components such as oxygen and carbon dioxide.

The products of the catalytic oxidation of ethane, ethylene and acetic acid, may be reacted in downstream processes to produce alkyl carboxylates such as ethyl acetate or alkenyl carboxylates such as vinyl acetate.

In view of the above there remains the need for an alternative and/or improved process for separating alkenes from a gas mixture comprising said alkenes, alkanes and oxygen.

We have now found that alkene may be separated from a gas mixture comprising said alkene, alkane and oxygen without the need for prior removal of the oxygen.

In addition, we have found that the separation of alkene from a gas mixture comprising said alkene, alkane and oxygen may be carried out in fewer processing stages than is required by the prior art.

Accordingly the present invention provides a process for separating an alkene from a gas mixture comprising said alkene, an alkane and at least 0.1 mol % oxygen which process comprises the steps:

(a) contacting said gas mixture with a solution of a metallic salt capable of selectively chemically absorbing the alkene to produce a chemically absorbed alkene-rich liquid stream;

(b) recovering the alkene from the metallic salt solution.

Advantageously, the process of the present invention, avoids the need for costly and energy intensive distillation separation apparatus.

Furthermore, the process of the present invention eliminates or at least mitigates the need for expensive refrigeration equipment.

More advantageously, the process of the present invention allows the safe separation of alkene from alkane in the presence of oxygen.

The process of the present invention is particularly useful for the separation of the alkene from the alkanes where the alkene and alkane being separated contain the same number of carbon atoms.

The process of the present invention is especially useful for separating ethylene from gas mixtures containing ethylene, ethane and oxygen.

In the process of the present invention, the alkane is preferably a $C_2$ to $C_4$ alkane or mixtures thereof such as ethane, propane, butane and mixtures thereof.

Preferably, the alkene is a $C_2$ to $C_4$ alkene or mixtures thereof such as ethylene, the propenes, the butenes and mixtures thereof.

The concentration of oxygen present in the gas mixture is at least 0.1 mol %, such as at least 0.2 mol %. Suitably, the concentration of oxygen in the gas mixture is in the range of 0.1 mol % up to a concentration where the gas mixture is below the flammable range. The oxygen concentration in the mixture must be such that the alkane-rich product stream is also non-flammable. It will be known to those skilled in the art that the limit of the flammable range is partly dependent on the pressure and temperature of the mixture. The gas mixtures of the process of the present invention should not enter the flammable range at any stage in the process. The gas separation process may be advantageously operated such that a gas mixture is as close as possible to the flammable range whilst remaining non-flammable.

Suitably, the concentration of oxygen in the gas mixture is 0.1 to 10 mol %, such as 0.2 to 8 mol %, for example, 0.2 to 6 mol %.

The separation process of present invention is especially applicable to product streams of chemical processes. Thus, the process of the present invention is particularly useful for separating alkenes from a gas mixture of alkenes, alkanes and oxygen produced in the oxidation of a $C_2$ to $C_4$ alkane.

Accordingly, the present invention provides a process for the oxidation of a $C_2$ to $C_4$ alkane to produce the corresponding alkene and carboxylic acid which process comprises the steps a) contacting in an oxidation reaction zone, said alkane, molecular oxygen-containing gas, optionally the corresponding alkene and optionally water, in the presence of at least one catalyst active for the oxidation of the alkane to the corresponding alkene and carboxylic acid, to produce a first product stream comprising alkene, carboxylic acid, alkane, oxygen and water;

b) separating in a first separation means at least a portion of the first product stream into a gaseous stream comprising alkene, alkane and oxygen and a liquid stream comprising carboxylic acid;

c) contacting said gaseous stream with a solution of a metallic salt capable of selectively chemically absorbing the alkene to produce a chemically absorbed alkene-rich liquid stream;

d) recovering an alkene-rich stream from the metallic salt solution.

The process of the present invention is also particularly useful when the alkene and/or carboxylic acid products of the oxidation process are used at least in part in integrated downstream processes, for example (a) for the production of ester by reacting the carboxylic acid with the alkene or an alcohol or (b) for the production of alkenyl carboxylate by the reaction of an oxygen-containing gas with the carboxylic acid and alkene. Alkene and/or carboxylic acid may be recovered from the product of the oxidation reaction zone and/or additional alkene and/or carboxylic acid may be used in the downstream process.

Accordingly, the present invention provides an integrated process for the production of an alkyl carboxylate which process comprises the steps:

(a) contacting in an oxidation reaction zone, an alkane, molecular oxygen-containing gas, optionally the corresponding alkene and optionally water, in the presence of at least one catalyst active for the oxidation of the alkane to the corresponding alkene and carboxylic acid, to produce a first non-flammable product stream comprising alkene, carboxylic acid, alkane, oxygen and water;

(b) separating in a first separation means at least a portion of the first product stream into a gaseous stream comprising alkene, alkane and oxygen and a liquid stream comprising carboxylic acid;

(c) contacting at least a portion of said gaseous stream with a solution of a metallic salt capable of selectively chemically absorbing the alkene to produce a chemically absorbed alkene-rich liquid stream;

(d) recovering an alkene-rich stream from the metallic salt solution and;

(e) contacting in a second reaction zone at least a portion of said alkene-rich stream from step (d), and a carboxylic acid, in the presence of at least one catalyst active for the production of alkyl carboxylate to produce said alkyl carboxylate, Also, in another embodiment, the present invention provides an integrated process for the production of an alkenyl carboxylate which process comprises the steps:

(a) contacting in an oxidation reaction zone, an alkane, molecular oxygen-containing gas, optionally the corresponding alkene and optionally water, in the presence of at least one catalyst active for the oxidation of the alkane to the corresponding alkene and carboxylic acid, to produce a first non-flammable product stream comprising alkene, carboxylic acid, alkane, oxygen and water;

(b) separating in a first separation means at least a portion of the first product stream into a gaseous stream comprising alkene, alkane and oxygen and a liquid stream comprising carboxylic acid;

(c) contacting at least a portion of said gaseous stream with a solution of a metallic salt capable of selectively chemically absorbing the alkene to produce a chemically absorbed alkene-rich liquid stream;

(d) recovering an alkene-rich stream from the metallic salt solution and;

(e) contacting in a second reaction zone at least a portion of said alkene-rich stream obtained in step (d), a carboxylic acid and a molecular oxygen-containing gas, in the presence of at least one catalyst active for the production of alkenyl carboxylate to produce said alkenyl carboxylate.

The separation process of the present invention will now be described in relation to the oxidation of a $C_2$ to $C_4$ alkane to produce a product stream comprising the corresponding alkene, alkane and oxygen and integrated processes thereof.

In the oxidation reaction, the $C_2$ to $C_4$ alkane is preferably ethane, the corresponding alkene being ethylene and the corresponding carboxylic acid being acetic acid. These products may be reacted in downstream processes to produce ethyl acetate or, with a molecular oxygen-containing gas to produce vinyl acetate.

Typically, the oxidation reaction is performed heterogeneously with solid catalysts and the reactants in the fluid phase. In this case, the concentrations of optional alkene and optional water may be controlled as partial pressures in the oxidation reaction zone.

Catalysts active for the oxidation of alkane to alkene and carboxylic acid may comprise any suitable catalysts known in the art, for example, for the oxidation of ethane to ethylene and acetic acid as described in U.S. Pat. No. 4,596,787, EP-A-0407091, DE 19620542, WO 99/20592, DE 19630832, WO 98/47850, WO 99/51339, EP-A-0 1043064, WO 9913980, U.S. Pat. No. 5,300,682 and U.S. Pat. No. 5,300,684, the contents of which are hereby incorporated by reference.

U.S. Pat. No. 4,596,787 relates to a process for the low temperature oxydehydrogenation of ethane to ethylene using a catalyst having the empirical formula $Mo_aV_bNb_cSb_dX_e$ as therein defined, the elements being present in combination with oxygen.

EP-A-0407091 relates to process and catalyst for the production of ethylene and/or acetic acid by oxidation of ethane and/or ethylene in the presence of an oxidation catalyst comprising molybdenum, rhenium and tungsten.

DE 19620542 relates to molybdenum, palladium, rhenium based oxidation catalysts for the production of acetic acid from ethane and/or ethylene.

WO 99/20592 relates to a method of selectively producing acetic acid from ethane, ethylene or mixtures thereof and oxygen at high temperature in the presence of a catalyst having the formula $Mo_aPd_bX_cY_d$ wherein X represents one or several of Cr, Mn, Nb, Ta, Ti, V, Te and W; Y represents one or several of B, Al, Ga, In, Pt, Zn, Cd, Bi, Ce, Co, Rh, Ir, Cu, Ag, Au, Fe, Ru, Os, K, Rb, Cs, Mg, Ca, Sr, Ba, Nb, Zr, Hf, Ni, P, Pb, Sb, Si, Sn, Tl and U and a=1, b=0.0001 to 0.01, c=0.4 to 1 and d=0.005 to 1.

German patent application DE 196 30 832 A1 relates to a similar catalyst composition in which a=1, b>0, c>0 and d=0 to 2. Preferably, a=1, b=0.0001 to 0.5, c=0.1 to 1.0 and d=0 to 1.0.

WO 98/47850 relates to a process for producing acetic acid from ethane, ethylene or mixtures thereof and a catalyst having the formula $W_aX_bY_cZ_d$ in which X represents one or several of Pd, Pt, Ag and Au, Y represents one or several of V, Nb, Cr, Mn, Fe, Sn, Sb, Cu, Zn, U, Ni, and Bi and Z represents one or several of Li, Na, K, Rb, Cs, Be, Mg, Ca, Sr, Ba, Sc, Y, La, Ti, Zr, Hf, Ru, Os, Co, Rh, Ir, B, Al, Ga, In, Tl, Si, Ge, Pb, P, As and Te, a=1, b>0, c>0 and d is 0 to 2.

WO 99/51339 relates to a catalyst composition for the selective oxidation of ethane and/or ethylene to acetic acid which composition comprises in combination with oxygen the elements $Mo_aW_bAg_cIr_dX_eY_f$ wherein X is the elements Nb and V; Y is one or more elements selected from the group consisting of Cr, Mn, Ta, Ti, B, Al, Ga, In, Pt, Zn, Cd, Bi, Ce, Co, Rh, Cu, Au, Fe, Ru, Os, K, Rb, Cs, Mg, Ca, Sr, Ba, Zr, Hf, Ni, P, Pb, Sb, Si, Sn, Tl, U, Re and Pd; a, b, c, d, e and f represent the gram atom ratios of the elements such that $0<a\leq1$, $0\leq b<1$ and $a+b=1$; $0<(c+d)\leq0.1$; $0<e\leq2$; and $0\leq f\leq2$.

EP-A-1043064 relates to a catalyst composition for the oxidation of ethane to ethylene and/or acetic acid and/or for the oxidation of ethylene to acetic acid which composition comprises in combination with oxygen the elements molybdenum, vanadium, niobium and gold in the absence of palladium according to the empirical formula: $Mo_aW_bU_cV_dNb_eY_f$ wherein Y is one or more elements selected from the group consisting of: Cr, Mn, Ta, Ti, B, Al, Ga, In, Pt, Zn, Cd, Bi, Ce, Co, Rh, Ir, Cu, Ag, Fe, Ru, Os, K, Rb, Cs, Mg, Ca, Sr, Ba, Zr, Hf, Ni, P, Pb, Sb, Si, Sn, Tl, U, Re, Te and La; a, b, c, d, e and f represent the gram atom ratios of the elements such that: $0<a\leq1$; $0\leq b<1$ and $a+b=1$; $10^{-5}<c\leq0.02$; $0<d\leq2$; $0<e\leq1$; and $0\leq f\leq2$.

WO 99/13980 relates to a catalyst for the selective oxidation of ethane to acetic acid of formula: $Mo_aV_bNb_cX_d$ wherein X is at least one promoter element selected from the group consisting of P, B, Hf, Te and As; a is a number ranging from about 1 to about 5; b is 1; c is a number ranging from about 0.01 to about 0.5; and d is a number ranging from greater than 0 to about 0.1.

U.S. Pat. No. 5,300,682 relates to the use of oxidation catalyst with empirical formula of $VP_aM_bO_x$ where M is one or more of Co, Cu, Re, Fe, Ni, Nb, Cr, W, U, Ta, Ti, Zr, Hf, Mn, Pt, Pd, Sn, Sb, Bi, Ce, As, Ag and Au, a is 0.5 to 3, b is 0 1 and x satisfies the valence requirements.

U.S. Pat. No. 5,300,684 relates to a fluid bed oxidation reaction using for example $Mo_{0.37}Re_{0.25}V_{0.26}Nb_{0.07}Sb_{0.03}Ca_{0.02}O_x$.

Other suitable oxidation catalysts for use in the present invention are described in WO 99/13980 which relates to the use of catalysts with elements in combination with oxygen in the relative gram atom ratios of $MO_aV_bNb_cX_d$ where X=P, B, Hf, Te or As; U.S. Pat. No. 6,030,920 which relates to the use of catalysts with elements in combination with oxygen in the relative gram atom ratios of $Mo_aV_bNb_cPd_d$; WO 00/00284 which relates to the use of catalysts with elements in combination with oxygen in the relative gram atom ratios of $Mo_aV_b$-$Nb_cPd_d$ and/or $Mo_aV_bLa_cPd_d$; U.S. Pat. No. 6,087,297 which relates to the use of catalysts with elements in combination with oxygen in the relative gram atom ratios of $Mo_aV_bPd_cLa_d$; WO 00/09260 which relates to the use of catalysts with elements in combination with oxygen in the relative gram atom ratios of $Mo_aV_bLa_cPd_dNb_eX_f$ where X=Cu or Cr and e and f can be zero; WO 00/29106 and WO 00/29105 which relate to the use of catalysts with elements in combination with oxygen in the relative gram atom ratios of $Mo_aV_bGa_cPd_dNb_eX_f$ wherein X=La, Te, Ge, Zn, Si, In or W and WO 00/38833 which relates to the use of catalysts with elements in combination with oxygen in the relative gram atom ratios of $Mo_aV_bLa_cPd_dNb_eX_f$ wherein X=Al, Ga, Ge or Si, the contents of which are hereby incorporated by reference.

Solid catalysts active for the oxidation of the $C_2$ to $C_4$ alkane may be supported or unsupported. Examples of suitable supports include silica, diatomaceous earth, montmorillonite, alumina, silica alumina, zirconia, titania, silicon carbide, activated carbon and mixtures thereof.

Solid catalysts active for the oxidation of the $C_2$ to $C_4$ alkane may be used in the form of a fixed or fluidised bed.

The oxidation catalyst would be expected to oxidise at least part of any alkene fed to the oxidation reaction zone, for example to the corresponding carboxylic acid.

The molecular oxygen-containing gas used in the oxidation reaction zone, may be air or a gas richer or poorer in molecular oxygen than air. A suitable gas may be, for example, oxygen diluted with a suitable diluent, for example nitrogen, argon or carbon dioxide. Preferably, the molecular oxygen-containing gas is oxygen. The molecular-oxygen containing gas may be fed to the oxidation reaction zone as a single feed stream comprising the alkane feed. Such an alkane/molecular-oxygen gas stream may be obtained from the separation of the alkene from alkene/alkane/molecular oxygen gas mixture.

Preferably, at least some of the molecular oxygen-containing gas is fed to the oxidation reaction zone independently from the alkane and optional alkene feeds, and any recycle streams.

Suitably, the concentration of the molecular-oxygen containing gas (as fresh feed and/or recycle) is such that the concentration of oxygen is from greater than 0 and up to and including 20 mol % of the total feed, including recycles, to the oxidation reaction zone, preferably 2-15 mol %.

The alkane and alkene fed into the oxidation reaction zone may be substantially pure or may be admixed, for example, with one or more of nitrogen, argon, methane, carbon dioxide, carbon monoxide, hydrogen, and low levels of other $C_2$ to $C_4$ alkenes/alkanes.

Suitably, the concentration of alkene (as fresh feed and/or recycle component) is from 0 and up to and including 50 mol % of the total feed, including recycles, to the oxidation reaction zone, preferably from 1 to 20 mol %, more preferably from 1 to 15 mol %.

Suitably, the concentration of water (as fresh feed and/or recycle component) is from 0 to 50 mol % inclusive of the total feed, including recycles, to the oxidation reaction zone, preferably from 0 to 25 mol %.

In one embodiment of the present invention, the alkene, such as ethylene, and water are co-fed into the oxidation reaction zone.

Suitably, the alkene, for example, ethylene, and water may be used in a ratio of 1:0.1-250 by weight, such as 1:0.1-100 or 1:0.1-50 but preferably in a ratio 1:0.1-10 by weight.

When solid catalysts are used in the oxidation reaction zone, the alkane, corresponding alkene, molecular-oxygen containing gas, optional water and any recycle gases are preferably passed through the oxidation reaction zone with a residence time corresponding to a combined gas hourly space velocity (GHSV) of 500-10,000 $hr^{-1}$; the GHSV being defined as volume (calculated at STP) of gas passing through the reactor divided by the bulk volume of settled catalyst.

The oxidation reaction may suitably be carried out at a temperature in the range from 100 to 400° C., typically in the range 140 to 350° C.

The oxidation reaction may suitably be carried out at atmospheric or superatmospheric pressure, for example, in the range from 5 to 27 barg.

Typically, alkane conversions in the range 1 to 99% may be achieved in the oxidation reaction of the present invention.

Typically, oxygen conversions in the range 30 to 99.99% may be achieved in the oxidation reaction of the present invention.

The concentration of oxygen in the product stream will depend to some extent on the degree of alkane conversion and the degree of selectivity to products. A high alkane conversion will result in a low concentration of oxygen present in the product stream. A high selectivity to product alkene will result in a high concentration of oxygen in the product stream.

The maximum (safe) concentration of oxygen in the product stream is determined by the flammable range of the oxygen to alkane ratio after separation of the alkene therefrom.

Thus, although the concentration of oxygen present in the product stream from the oxidation reaction zone may be less than 0.1 mol % it is typically at least 0.1 mol %, such as at least 0.2 mol %. Suitably, provided the product stream is non-flammable, the concentration of oxygen in the product stream is in the range of 0.1 mol % up to and including 10 mol %, such as 0.2 to 8 mol %, for example, 0.2 to 6 mol %.

In the oxidation reaction, the catalyst suitably has a productivity in the range 10 to 10000 grams of carboxylic acid, such as acetic acid, per hour per kilogram of catalyst.

In the oxidation reaction, the catalyst suitably has a productivity in the range 5 to 5000 grams of alkene, such as ethylene, per hour per kilogram of catalyst.

Carbon monoxide can have an adverse effect on some catalysts used in the production of vinyl acetate. Thus, depending on the nature of the catalyst employed, it is desirable that the first product stream should have a low concentration of carbon monoxide by-product.

Thus, it is also preferred to use a catalyst in the oxidation reaction zone that gives negligible carbon monoxide by-product. An additional catalyst component in the oxidation reaction zone may be used to oxidise carbon monoxide to carbon dioxide. The additional catalyst component may be present in the oxidation catalyst or catalysts or in a secondary reaction zone or may be present as a separate catalyst in the oxidation reaction zone.

When ethane is used as a reactant for the oxidation reaction, the product stream comprises acetic acid, ethylene, unreacted ethane, oxygen and water and may also contain inert gas components such as argon and nitrogen and the by-products, acetaldehyde, carbon monoxide and carbon dioxide. Acetaldehyde and carbon monoxide may be converted by the molecular oxygen-containing gas to produce acetic acid and carbon dioxide respectively, either in downstream processes or, after recycling, in the oxidation reaction zone.

Ethylene is present in the product stream of the oxidation reaction as unconverted reactant ethylene from the feed and/or as oxidation product of the ethane reactant.

The product stream from the oxidation reaction zone is separated in a first separation means into a gaseous stream comprising the alkene, unreacted alkane and oxygen and a liquid stream comprising the carboxylic acid. Any suitable separation means known in the art may be employed such as a membrane separation unit, condensing unit or a distillation unit. Preferably, the separation means employed is a condenser.

Where the product stream from the oxidation reaction comprises acetic acid, ethylene, ethane, oxygen and water, the product stream may be, and is preferably, separated by condensation into an overhead gaseous stream comprising ethylene, ethane and oxygen and a base liquid stream comprising acetic acid and water. In general, the gaseous stream will also comprise carbon oxides such as carbon dioxide.

Optionally, carboxylic acid and/or alkene may be recovered from the product stream of the oxidation reaction.

The gaseous stream from the first separation means is contacted with a solution of a metal salt capable of selectively chemically absorbing the alkene to produce a chemically absorbed alkene-rich liquid stream.

Suitable metallic salts are those capable of forming a complex with the alkene.

Where, the alkene is ethylene, suitable metal salts comprise, chromium, copper (I), manganese, nickel, iron, mercury, silver, gold, platinum, palladium, rhodium, ruthenium, osmium, molybdenum, tungsten and rhenium.

Preferably, the metal salt comprises silver or copper (I), most preferably silver.

Where the metal salt is a silver salt, the silver salt is preferably, silver nitrate or silver fluoroborate.

Where the metal salt is a copper (I) salt, the copper (I) salt is preferably copper (I) acetate, copper (I) nitrate or copper (I) sulphate, most preferably copper (I) nitrate.

The metal solution may be aqueous or may comprise an organic nitrogen-containing compound such as pyridine, piperidine, hydroxy-propionitrile, diethylenetriamine, acetonitrile, formamide, acetamide and derivatives thereof.

Preferably, the metallic salt solution is an aqueous solution.

Where the metal salt is copper (I), the concentration of metal salt to nitrogen-containing compound is suitably in the range 1:1 to 1:6, preferably, 1:2.

The concentration of metal salt in the solution is suitably at least 0.5 moles of metal salt per litre of solvent, preferably, at least 2 moles of metal salt per litre of solvent.

Neither the alkane nor the oxygen present in the gaseous stream forms a complex with the metallic salt solution to any significant extent.

The contacting of the gaseous stream with the metallic salt solution may be carried out in any suitable means such as in an absorber column. The absorber column may be fitted with trays or packing such as raschig rings or structured packing. Preferably, the absorber column is fitted with packing.

To improve the purity of the alkene, the absorber column is suitably equipped with a reboiler.

Preferably, the absorber column is operated with counter-current flow of gas and metallic salt solution.

Suitably, the contacting may be carried out at a temperature in the range from −10 to 300° C., preferably, 0 to 100° C.

Suitably, the contacting may be carried out at a pressure in the range from 1 to 70 barg, preferably, 3 to 30 barg.

Where the contacting is carried out in an absorber column, the metallic salt solution comprising the metal salt/alkene complex may be removed from the base of the absorber.

As the alkane and oxygen do not complex to any significant extent with the metallic salt solution they are removed as an overhead stream from the absorber column.

Trace amounts of oxygen and/or alkane absorbed in the metallic salt solution are mostly removed from the solution with the alkene.

An alkene-rich stream may be recovered from the metallic salt solution by heat, reduced pressure or by a combination thereof. Preferably, the solution is subjected to a reduced pressure such that the complex decomposes to release the alkene.

The pressure used for recovery of the alkene-rich stream from the metallic salt solution may be 2 to 98% of the absolute pressure used to form the metal salt/alkene complex, preferably 10 to 80% of the absolute pressure used to form the complex.

Alternatively, the alkene-rich stream may be recovered from the metallic salt solution by degassing at a temperature in the range from 0 to 80° C., preferably in the range 15 to 35° C. above the temperature of formation of the complex.

The alkene-rich stream may also be recovered from the solution using a combination of reduced pressure and increased temperature.

The pressure reduction may be carried out in one or more stages, for example, in one or more flashing apparatus.

Where one or more flashing apparatus are employed, the alkene-rich stream is removed therefrom as an overhead stream. The overhead stream may be compressed prior to be being optionally dried. Alternatively, the overhead stream may be dried prior to being compressed. Where the alkene-rich stream is compressed, it may be compressed to a pressure suitable for feeding to the second reaction zone. Suitably, it may be compressed to the pressure of any additional alkene feed to the second reaction zone.

The alkene-free complex may be recycled for re-use in the absorber.

The alkene-rich stream will comprise the alkene and may comprise low levels of alkane and oxygen and other impurities such as carbon dioxide.

Suitably, the alkene-rich stream, such as an ethylene-rich stream, comprises at least 50% alkene, such as at least 80% alkene. Preferably the alkene-rich stream comprises at least 90% alkene, more preferably, 95% alkene, and most preferably, at least 99% alkene.

The alkene-rich stream may be recovered from the metallic salt solution in one or more absorption/desorption stages, such as one absorption and two desorption stages.

Advantageously, the use of an alkene feed to the second reaction zone having reduced levels of impurities allows the amount of purge gas which has to be vented from the second reaction zone to be reduced and hence the loss of alkene from the second reaction zone is also reduced.

The alkane and oxygen stream (alkane-rich stream) may comprise low levels of alkene and other impurities such as carbon dioxide. The alkane-rich stream must be non-flammable. The flammable range will depend on, for example, temperature and pressure of the alkane-rich stream, however, typically, the oxygen concentration in the alkane-rich stream may be in the range 0.1 to 10 mol %.

In a preferred embodiment of the process of the present invention, the alkene/alkane/oxygen gaseous stream (gaseous stream from the first separation means), prior to being contacted with the metallic salt solution, is treated to remove components such as carbon dioxide, and oxygenates such as acetaldehyde.

The alkane and oxygen containing gas stream may be fed as one or more streams to the oxidation reaction zone together with additional alkane.

Optionally, prior to being fed into the oxidation reaction zone, the alkane and oxygen containing stream may be separated into separate alkane and oxygen gas streams.

The additional alkane may be fresh alkane and/or may be unreacted alkane from the oxidation reaction zone which has been recycled after the first separation means to the oxidation reaction zone.

The alkane/oxygen stream and additional alkane may be introduced into the oxidation reaction zone either as separate feed streams or as a single feed stream comprising both the alkane/oxygen and additional alkane.

The alkene-rich stream is fed as one or more streams, to a second reaction zone together with additional molecular oxygen-containing gas, optional additional alkene and carboxylic acid to produce alkenyl carboxylate, such as vinyl acetate.

The alkene-rich stream and additional alkene may be introduced into the second reaction zone either as separate feed streams or as a single feed stream comprising both alkene-rich stream and additional alkene.

The additional alkene may be fresh alkene and/or recycled alkene from the second reaction zone and/or a portion of the alkane/alkene stream from the oxidation reaction zone.

Additional alkene introduced into the second reaction zone for the production of alkenyl carboxylate may be substantially pure or may be admixed, for example, with one or more of nitrogen, argon, methane, carbon dioxide, carbon monoxide, hydrogen, and low levels of other $C_2$ to $C_4$ alkenes/alkanes.

Suitably, the concentration of alkene (optional additional alkene feed and alkene-rich stream feed), such as ethylene, fed to the second reaction zone is at least 50 mol % of the total feed to the second reaction zone, preferably, at least 55 mol %, more preferably at least 60 mol %. Suitably, the concentration of alkene is up to 85 mol % of the total feed to the second reaction zone, preferably, in the range at least 50 mol % to 80 mol %, such as at least 55 mol % to 80 mol %.

Catalysts known in the art for the production of alkenyl carboxylates may be used in the process of the present invention. Thus, catalyst active for the production of vinyl acetate which may be used in a second reaction zone of the present invention may comprise, for example, catalysts as described in GB 1 559 540; U.S. Pat. No. 5,185,308 and EP-A-0672453 the contents of which are hereby incorporated by reference.

GB 1 559 540 describes a catalyst active for the preparation of vinyl acetate by the reaction of ethylene, acetic acid and oxygen, the catalyst consisting essentially of: (1) a catalyst support having a particle diameter of from 3 to 7 mm and a pore volume of from 0.2 to 1.5 ml/g, a 10% by weight water suspension of the catalyst support having a pH from 3.0 to 9.0, (2) a palladium-gold alloy distributed in a surface layer of the catalyst support, the surface layer extending less than 0.5 mm from the surface of the support, the palladium in the alloy being present in an amount of from 1.5 to 5.0 grams per litre of catalyst, and the gold being present in an amount of from 0.5 to 2.25 grams per litre of catalyst, and (3) from 5 to 60 grams per litre of catalyst of alkali metal acetate.

U.S. Pat. No. 5,185,308 describes a shell impregnated catalyst active for the production of vinyl acetate from ethylene, acetic acid and an oxygen containing gas, the catalyst consisting essentially of: (1) a catalyst support having a particle diameter from about 3 to about 7 mm and a pore volume of 0.2 to 1.5 ml per gram, (2) palladium and gold distributed in the outermost 1.0 mm thick layer of the catalyst support particles, and (3) from about 3.5 to about 9.5% by weight of potassium acetate wherein the gold to palladium weight ratio in said catalyst is in the range 0.6 to 1.25.

EP-A-0672453 describes palladium containing catalysts and their preparation for fluid bed vinyl acetate processes.

Typically, the production of alkenyl carboxylate such as vinyl acetate in the second reaction zone is carried out heterogeneously with the reactants being present in the gas phase.

The molecular oxygen-containing gas used in the second reaction zone for the production of alkenyl carboxylate may comprise unreacted molecular oxygen-containing gas from step (a) and/or additional molecular oxygen-containing gas.

The additional molecular oxygen-containing gas, if used, may be air or a gas richer or poorer in molecular oxygen than air. A suitable additional molecular oxygen-containing gas may be, for example, oxygen diluted with a suitable diluent, for example nitrogen, argon or carbon dioxide. Preferably, the additional molecular oxygen-containing gas is oxygen. Preferably, at least some of the molecular oxygen-containing gas is fed independently to the second reaction zone from the alkene and carboxylic acid reactants.

The carboxylic acid fed to the second reaction zone for the production of alkenyl carboxylate may comprise fresh and/or recycle acid. Preferably, at least a portion of the carboxylic acid introduced in to the second reaction zone comprises carboxylic acid produced from the oxidation reaction zone.

The fresh and recycle carboxylic acid may be introduced into the second reaction zone either as separate feed streams or as a single feed stream comprising both fresh and recycle acid.

The carboxylic acid fed to the second reaction zone for the production of alkenyl carboxylate may comprise at least a portion of the acid obtained from downstream processes such as from the separation of the acid from a mixture of the acid/alkenyl carboxylate/water.

At least part of the carboxylic acid fed to the second reaction zone may be liquid.

When solid catalysts are used in the second reaction zone for the production of alkenyl carboxylate, the alkene from the second separation means, the carboxylic acid from the oxidation reaction zone, any additional alkene or carboxylic acid reactants, any recycle streams and molecular oxygen-containing gas are preferably passed through the second reaction zone at a combined gas hourly space velocity (GHSV) of 500-10,000 $hr^{-1}$.

The second reaction zone for the production of alkenyl carboxylate may suitably be operated at a temperature in the range from 140 to 200° C.

The second reaction zone for the production of alkenyl carboxylate may suitably be operated at a pressure in the range 50 to 300 psig.

The second reaction zone for the production of alkenyl carboxylate may suitably be operated as either a fixed or a fluidised bed process.

Carboxylic acid conversions in the range 5 to 80% may be achieved in the second reaction zone for the production of alkenyl carboxylate.

Oxygen conversions in the range 20 to 100% may be achieved in the second reaction zone for the production of alkenyl carboxylate.

Alkene conversions in the range 3 to 100% may be achieved in the second reaction zone for the production of alkenyl carboxylate.

In the second reaction zone for the production of alkenyl carboxylate, the catalyst suitably has a productivity in the range 10 to 10000 grams of alkenyl carboxylate per hour per kg of catalyst.

When the alkane used in the process of the present invention is ethane, the product stream from the second reaction zone for the production of alkenyl carboxylate may comprise vinyl acetate, water and acetic acid and optionally also unreacted ethylene, ethane, oxygen, acetaldehyde, nitrogen, argon, carbon monoxide and carbon dioxide. Such a product stream may be separated by azeotropic distillation into an overhead fraction comprising vinyl acetate and water and a base fraction comprising acetic acid and water. The base fraction is be removed from the distillation column as liquid from the bottom of the column. In addition, a vapour from one or more stages above the bottom of the column may also be removed. Prior to such a distillation step, ethylene, ethane, acetaldehyde, carbon monoxide and carbon dioxide, if any, may be removed from the second product stream, suitably as an overhead gaseous fraction from a scrubbing column, in which a liquid fraction comprising vinyl acetate, water and acetic acid is removed from the base. The ethylene and/or ethane may be recycled to the oxidation reaction zone and/or the second reaction zone and/or the second separation means.

The alkenyl carboxylate, for example, vinyl acetate is recovered from the overhead fraction, suitably for example by decantation. The recovered alkenyl carboxylate, such as vinyl acetate, may, if desired, be further purified in known manner.

The base fraction comprising carboxylic acid, such as acetic acid and water may be recycled, with or preferably without further purification, to the second reaction zone. Alternatively, the carboxylic acid is recovered from the base fraction and may be further purified if desired, in known manner, for example by distillation.

The invention will now be illustrated by reference to the FIGURE.

The FIGURE represents in schematic block-diagram, apparatus suitable for use in a process of the present invention.

The apparatus comprises an oxidation reaction zone (1) provided with a supply of ethane and optionally ethylene (3), a supply of a molecular oxygen-containing gas (4), a supply of recycle gas comprising ethane and ethylene (5), a supply (19) of ethane and oxygen from an ethylene/ethane/oxygen absorber column (21), and an outlet (18) for a first product stream. Depending on the scale of the process, the oxidation reaction zone (1) may comprise either a single reactor or several reactors in parallel or series.

The apparatus also comprises a scrubber (6) for separating the first product stream into a gaseous stream comprising ethylene, ethane and carbon oxides and a liquid stream comprising acetic acid and water. Optionally, the apparatus comprises means (not shown) for removing water from the acetic acid, such as a distillation unit.

The apparatus also comprises a series of flashing apparatus (flashing valves and drums) (22,23) for subjecting the ethylene/metallic salt complex obtained as a base fraction from absorber column (21) to a reduced pressure and an optional compressor (24) for compressing an ethylene-rich overhead stream from the flashing apparatus (22, 23).

The apparatus also comprises a second reaction zone (2) for acetoxylation of ethylene to vinyl acetate which is provided with means (17) for conveying at least a portion of the acetic acid from the scrubber (6) into the second reaction zone, optionally via a means for removing water from the liquid stream, a supply of molecular oxygen-containing gas (9), a supply of recycle acetic acid (10), an optional supply or supplies of acetic acid and/or ethylene (8) and a supply (25) of ethylene from the optional compressor (24). Depending on the scale of the process, the second reaction zone (2) may comprise either a single reactor or several reactors in parallel or in series.

The apparatus further comprises a scrubber (12) for the product from the second reaction zone; means (13) for separating acetic acid from the product of the second reaction zone; vinyl acetate purfication means (14); optional acetic acid purification means (15) and one or more separation means (16) for separating carbon dioxide from the gaseous stream obtained from scrubber (6) and optionally for recovery of ethylene product.

In use, the oxidation reaction zone (1) is provided with at least one catalyst each active for the oxidation of the ethane to form acetic acid and ethylene. Suitably the oxidation catalysts are solid catalysts. Molecular oxygen-containing gas is fed to the oxidation reaction zone (1) from supply (4) through one or more inlets. A gaseous feedstock comprising ethane and ethylene is fed to the oxidation reaction zone (1) from supply (3). Recycle gas comprising ethane and ethylene is also fed to the oxidation reaction zone (1) from supply (5). Ethane and oxygen from the absorber column (21) is fed to the oxidation reaction zone (1) from supply (19)

The molecular oxygen-containing gas, ethane, ethylene and recycle gas are introduced into the oxidation reaction zone (1) through one or more inlets separately or in partial or complete combination. Optionally at least one of the streams fed to the oxidation reactor also comprises water.

In the oxidation reactor a first product stream is produced which comprises ethylene (as product and/or unreacted feed), acetic acid, water, optionally unconsumed molecular oxygen-containing gas, unreacted ethane and by-products such as carbon monoxide, carbon dioxide, inerts and acetaldehyde. At least a portion of this product stream is passed to a scrubber (6) from which a gaseous stream comprising ethylene, ethane, oxygen and the carbon oxides and a liquid stream comprising acetic acid and water are removed. At least a portion of the gaseous stream is fed, after separating by-products such as carbon dioxide in separation means (16) and optionally recovering a portion of the ethylene product by methods known in the art, to a high pressure absorber column (21). At least a portion of a gaseous stream comprising ethylene and ethane from separation means (16) is recycled to the oxidation reaction zone (1) via supply (5). The gaseous stream comprising ethylene, ethane and oxygen is fed to the absorber column (21) which contains silver nitrate solution with which the ethylene reacts to form a silver nitrate/ethylene complex. The ethane and oxygen are not complexed and are removed as an overhead stream from the column. A solution containing the silver nitrate/ethylene complex is removed from the base of the absorber column. The solution is passed to a series of flash-drums (22, 23) where it is subjected to a reduced pressure. Under such conditions, the silver nitrate/ethylene complex decomposes releasing ethylene. Ethylene is recovered as an overhead stream. The overhead ethylene stream is fed to a compressor (24) prior to being fed via supply (25) to the second reaction zone (2). The ethane/oxygen stream from the absorber column is fed to the oxidation reaction zone (1) via supply (19)

Acetic acid may be recovered from the liquid stream of scrubber (6), for example by distillation.

At least a portion of the acetic acid from the liquid stream is fed by means (17), optionally via a water removal means (not shown), into the second reaction zone (2), which is provided with an acetoxylation catalyst, suitably a solid catalyst. A molecular oxygen-containing gas is fed to the second reaction zone from supply (9). Acetic acid is fed to the second reaction zone from recycle supply (10). Optionally, additional ethylene and/or acetic acid may be fed to the second reaction zone from supply or supplies (8). Ethylene is fed from the separation means (21) to the second reaction zone from supply (22). Acetic acid from the liquid scrubber stream, molecular oxygen-containing gas, recycle acetic acid, optional additional supplies of ethylene and/or acetic acid, and ethylene from the separation means (21) are fed into the second reaction zone through one or more inlets separately or in partial or complete combination.

In the second reaction zone the ethylene, acetic acid and molecular oxygen react to produce a second product stream comprising vinyl acetate.

The second reaction product is passed to scrubber (12) from which gas and liquid are separated. Carbon dioxide is separated from the gas and optionally ethylene product recovered, in one or more separation stages (not shown) by methods known in the art. The remaining ethylene and ethane may be recycled to the first and/or second reaction zones. Acetic acid is separated in separation means (13) from the scrubber liquid and is recycled to the second reaction zone via recycle supply (10). Optionally, acetic acid product may be recovered from the recycle stream by means (15), for example by distillation. Vinyl acetate product is recovered from the scrubber liquid by means (14), for example by distillation.

The invention claimed is:

1. A process for the oxidation of a $C_2$ to $C_4$ alkane to produce the corresponding alkene and carboxylic acid which process comprises the steps:
   (a) contacting in an oxidation reaction zone, an alkane, molecular oxygen-containing gas, optionally the corresponding alkene and optionally water, in the presence of at least one catalyst active for the oxidation of the alkane to the corresponding alkene and carboxylic acid, to produce a first product stream comprising alkene, carboxylic acid, alkane, oxygen and water;
   (b) separating in a first separation means at least a portion of the first product stream into a gaseous stream comprising alkene, alkane and oxygen and a liquid stream comprising carboxylic acid;
   (c) contacting said gaseous stream with a solution of a metallic salt capable of selectively chemically absorbing the alkene to produce a chemically absorbed alkene-rich liquid stream; and
   (d) recovering an alkene-rich stream from the metallic salt solution.

2. An integrated process for the production of an alkyl carboxylate which process comprises the steps:
   (a) contacting in an oxidation reaction zone, an alkane, molecular oxygen-containing gas, optionally the corresponding alkene and optionally water, in the presence of at least one catalyst active for the oxidation of the alkane to the corresponding alkene and carboxylic acid, to produce a first non-flammable product stream comprising alkene, carboxylic acid, alkane, oxygen and water;
   (b) separating in a first separation means at least a portion of the first product stream into a gaseous stream comprising alkene, alkane and oxygen and a liquid stream comprising carboxylic acid;
   (c) contacting at least a portion of said gaseous stream with a solution of a metallic salt capable of selectively chemically absorbing the alkene to produce a chemically absorbed alkene-rich liquid stream;
   (d) recovering an alkene-rich stream from the metallic salt solution; and
   (e) contacting in a second reaction zone at least a portion of said alkene-rich stream from step (d), and a carboxylic acid, in the presence of at least one catalyst active for the production of alkyl carboxylate to produce said alkyl carboxylate.

3. An integrated process for the production of an alkenyl carboxylate which process comprises the steps:
   (a) contacting in an oxidation reaction zone, an alkane, molecular oxygen-containing gas, optionally the corresponding alkene and optionally water, in the presence of at least one catalyst active for the oxidation of the alkane to the corresponding alkene and carboxylic acid, to produce a first non-flammable product stream comprising alkene, carboxylic acid, alkane, oxygen and water;
   (b) separating in a first separation means at least a portion of the first product stream into a gaseous stream comprising alkene, alkane and oxygen and a liquid stream comprising carboxylic acid;
   (c) contacting at least a portion of said gaseous stream with a solution of a metallic salt capable of selectively chemically absorbing the alkene to produce a chemically absorbed alkene-rich liquid stream;
   (d) recovering an alkene-rich stream from the metallic salt solution; and (e) contacting in a second reaction zone at least a portion of said alkene-rich stream obtained in step (d), a carboxylic acid and a molecular oxygen-containing gas, in the presence of at least one catalyst active for the production of alkenyl carboxylate to produce said alkenyl carboxylate.

4. The process according to claim 3, wherein, in step (e), said alkene-rich stream is fed to the second reaction zone as one or more streams, together with optional additional alkene.

5. The process according to claim 4, wherein the additional alkene may be fresh alkene and/or recycled alkene from the second reaction zone and/or a portion of the alkane/alkene stream from the oxidation reaction zone.

6. The process according to claim 3, wherein the concentration of alkene (optional additional alkene feed and alkene-rich stream feed) fed to the second reaction zone is at least 50 mol % of the total feed to the second reaction zone.

7. The process according to claim 6 wherein the concentration of alkene is at least 60 mol % of the total feed to the second reaction zone.

8. The process according to claim 6 wherein the concentration of alkene is up to 85 mol % of the total feed to the second reaction zone.

9. The process according to claim 3 wherein the molecular oxygen-containing gas used in the second reaction zone for the production of alkenyl carboxylate comprises unreacted molecular oxygen-containing gas from step (a) and/or additional molecular oxygen-containing gas.

10. The process according to claim 9, wherein the additional molecular oxygen-containing gas is oxygen.

11. The process according to claim 3 wherein at least some of the molecular oxygen-containing gas is fed independently to the second reaction zone from the alkene and carboxylic acid reactants.

12. The process according to claim 3 wherein the carboxylic acid introduced in to the second reaction zone comprises carboxylic acid produced from the oxidation reaction zone.

13. A process according to claim 1 wherein the alkane is selected from the group consisting of $C_2$ to $C_4$ alkanes and mixtures thereof.

14. A process according to claim 1 wherein the alkane is ethane, the corresponding alkene is ethylene and the corresponding carboxylic acid is acetic acid.

15. A process according to claim 1 wherein the molecular oxygen-containing gas in step (a) is oxygen.

16. The process according to claim 1 wherein the concentration of the molecular oxygen-containing gas (as fresh feed and/or recycle) is from greater than 0 to 20 mol % of the total feed, including recycles, to the oxidation reaction zone.

17. The process according to claim 1 wherein the concentration of alkene (as fresh feed and/or recycle component) is from 0 to 50 mol % of the total feed, including recycles, to the oxidation reaction zone.

18. The process according to claim 17, wherein the concentration of alkene is from 1 to 20 mol % of the total feed to the oxidation reaction zone.

19. The process according to claim 1 wherein the concentration of water (as fresh feed and/or recycle component) is from 0 to 50 mol % of the total feed, including recycles, to the oxidation reaction zone.

20. The process according to claim 19, wherein the concentration of water is from 0 to 25 mol % of the total feed to the oxidation reaction zone.

21. The process according to claim 1 wherein the alkene and water are co-fed into the oxidation reaction zone.

22. The process according to claim 1 wherein the alkene and water are used in a ratio of 1:0.1-250 by weight.

23. A process according to claim 1 wherein the concentration of oxygen present in the gaseous stream from the first separation means is at least 0.1 mol %.

24. A process according to claim 23, wherein the concentration of oxygen present in the gaseous stream from the first separation means is at least 0.2 mol %.

25. A process according to claim 24, wherein the concentration of oxygen present in the gaseous stream from the first separation means is 0.1 to 10 mol %.

26. A process according to claim 1 wherein the first separation means is a membrane separation unit, condensing unit or a distillation unit.

27. A process according to claim 26, wherein the separation means employed is a condenser.

28. The process according to claim 1 wherein the alkene is ethylene and the metal salt capable of selectively chemically absorbing the alkene comprises chromium, copper (I), manganese, nickel, iron, mercury, silver, gold, platinum, palladium, rhodium, ruthenium, osmium, molybdenum, tungsten or rhenium.

29. The process according to claim 28, wherein the metallic salt comprises silver or copper (I).

30. The process according to claim 29, wherein the metallic salt is a silver salt.

31. The process according to claim 30, wherein the silver salt is silver nitrate or silver fluoroborate.

32. The process according to claim 29, wherein the metallic salt is copper (I) acetate, copper (I) nitrate or copper (I) sulphate.

33. The process according to claim 1 wherein the metal solution is aqueous or comprises an organic nitrogen-containing compound.

34. The process according to claim 1 wherein the contacting of the gaseous stream from the first separation means with the metallic salt solution is carried out in an absorber column.

35. The process according to claim 34, wherein the metallic salt solution comprising the metal salt/alkene complex is removed from the base of the absorber column, and alkane and oxygen are removed as an overhead stream from the absorber column.

36. The process according to claim 35, wherein the alkane and oxygen containing gas stream is fed as one or more streams to the oxidation reaction zone together with additional alkane.

37. The process according to claim 36, wherein, prior to being fed to the oxidation reaction zone, the alkane and oxygen containing stream is separated into separate alkane and oxygen gas streams.

38. The process according to claim 36, wherein the additional alkane is fresh alkane and/or unreacted alkane from the oxidation reaction zone which has been recycled after the first separation means to the oxidation reaction zone.

39. The process according to claim 36 wherein the alkane/oxygen stream and the additional alkane are introduced into the oxidation reaction zone together either as separate feed streams or as a single feed stream comprising both the alkane/oxygen and the additional alkane.

40. The process according to claim 1 wherein the alkene-rich stream is recovered from the metallic salt solution complex by heat, reduced pressure or by a combination thereof.

41. The process according to claim 40, wherein the solution is subjected to a reduced pressure such that the complex decomposes to release the alkene.

42. The process according to claim 1 wherein the alkene-rich stream comprises at least 50% alkene.

43. The process according to claim 42, wherein the alkene-rich stream comprises at least 90% alkene.

44. The process according to claim 1 wherein the gaseous stream from the first separation means, prior to being contacted with the metallic salt solution, is treated to remove components selected from the group consisting of carbon dioxide and oxygenates.

45. Art integrated process for the production of vinyl acetate which process comprises the steps:
  (a) contacting in an oxidation reaction zone, ethane, molecular oxygen-containing gas, optionally ethylene and optionally water, in the presence of at least one catalyst active for the oxidation of ethane to ethylene and acetic acid, to produce a first non-flammable product stream comprising ethylene, acetic acid, ethane, oxygen and water;
  (b) separating in a first separation means at least a portion of the first product stream into a gaseous stream comprising ethylene, ethane and oxygen and a liquid stream comprising acetic acid;
  (c) contacting at least a portion of said gaseous stream with a solution or a metallic salt capable of selectively chemically absorbing ethylene to produce a chemically absorbed ethylene-rich liquid stream;
  (d) recovering an ethylene-rich stream from the metallic salt solution; and
  (e) contacting in a second reaction zone at least a portion of said ethylene-rich stream obtained in step (d), acetic acid and a molecular oxygen-containing gas, in the presence of at least one catalyst active for the production of vinyl acetate to produce vinyl acetate.

* * * * *